United States Patent [19]
Beaty

[11] Patent Number: 5,603,338
[45] Date of Patent: Feb. 18, 1997

[54] IMPLANT SURFACE PREPARATION UTILIZING ACID TREATMENT

[75] Inventor: Keith D. Beaty, Palm Beach Gardens, Fla.

[73] Assignee: Innovative Implants, Inc., West Palm Beach, Fla.

[21] Appl. No.: 650,594

[22] Filed: May 20, 1996

Related U.S. Application Data

[63] Continuation of Ser. No. 351,214, Nov. 30, 1994, abandoned.

[51] Int. Cl.⁶ .................................................. A61B 19/00
[52] U.S. Cl. ............................ 128/898; 623/16; 623/901; 427/2.24; 427/2.27; 433/201.1
[58] Field of Search ..................... 623/16, 901; 128/898; 433/201.1; 427/2.24, 2.26, 2.27

[56] References Cited

U.S. PATENT DOCUMENTS

| | | |
|---|---|---|
| 3,855,638 | 12/1974 | Pilliar . |
| 4,145,764 | 3/1979 | Suzuki et al. ................................. 3/1.9 |
| 4,818,559 | 4/1989 | Hama et al. . |
| 4,874,434 | 10/1989 | Riggs, Jr. ..................................... 134/3 |
| 4,908,030 | 3/1990 | Linkow et al. ............................. 623/16 |
| 4,911,953 | 3/1990 | Hosonuma et al. ..................... 427/2.27 |
| 4,944,754 | 7/1990 | Linkow et al. ............................ 623/16 |
| 5,071,351 | 12/1991 | Green et al. . |
| 5,188,800 | 2/1993 | Green et al. . |
| 5,190,795 | 3/1993 | Culler ........................................ 427/226 |
| 5,344,425 | 9/1994 | Sawyer ..................................... 606/198 |
| 5,456,723 | 10/1995 | Steinemann et al. ...................... 623/16 |
| 5,484,286 | 1/1996 | Hansson .............................. 433/201.1 |

FOREIGN PATENT DOCUMENTS

606566A1   7/1994   European Pat. Off. .

OTHER PUBLICATIONS

Albrektsson, T., P. I. Branemark, H. A. Hansson & J. Lindstrom, "Osseointegrated Titanium Implants," 1991.
"Step–Screw Implant," *Dental Products Report*, Mar. 1993.
"Ion–Beam–Sputter Modification of the Surface Morphology of Biological Imlants", *J. Vac. Soc. Technol*, vol. 14, No. 1, Jan./Feb. 1977, pp. 326–331.
"The Influence of Various Titanium Surfaces On The Interface Strength Between Implants and Bone," *Advances in Biomaterials*, vol. 9, pp. 309–314, Elsevier Science Publishers BV, Amsterdam, 1990.
"Influence of Surface Characteristics On Bone Integration of Titanium Implants", *Journal Of Biomedical Materials Research*, vol. 25, pp. 889–902, John Wiley & Sons, Inc., 1991.
"Short–term Plasma–cleaning Treatments Enhance In Vitro Osteoblast Attachment To Titanium", *Journal of Oral Implantology*, vol. XVIII, No. 2 (1992), pp. 130–137.
"Design and Surface Characteristics of 13 Commercially Available Oral Implant Systems," *Int. J. Oral Maxillofactial Implants*, 1993, 8:622–633.

*Primary Examiner*—Paul B. Prebilic
*Attorney, Agent, or Firm*—Arnold, White & Durkee

[57] ABSTRACT

The surface of a device that is surgically implantable in living bone is prepared. The device is made of titanium with a native oxide layer on the surface. The method of preparation comprises the steps of removing the native oxide layer from the surface of the device and performing further treatment of the surface substantially in the absence of unreacted oxygen.

15 Claims, 4 Drawing Sheets

IMPLANT SURFACE PREPARATION UTILIZING ACID TREATMENT

This application is a file wrapper continuation of application Ser. No. 08/351,214, filed Nov. 30, 1994, now abandoned.

FIELD OF THE INVENTION

The present invention relates to processes for improving the surfaces of devices to be surgically implanted in living bone, and to implant devices having the improved surfaces.

BACKGROUND OF THE INVENTION

The success of prosthetic devices surgically implanted in living bone depends substantially entirely on achieving and maintaining an enduring bond between the confronting surfaces of the device and the host bone. Surgical procedures for preparing living bone to receive a surgically implanted prosthetic device have been known for twenty years or more, but considerable controversy remains concerning the ideal properties of the surface of the device which confronts the host bone.

It is known through clinical experience extending over several decades that titanium and its dilute alloys have the requisite biocompatability with living bone to be acceptable materials for use in making surgically implantable prosthetic devices, when the site of installation is properly prepared to receive them. There is, however, less certainty about the ideal physical properties of the surfaces of the prosthetic devices which confront the host bone. For example, the endosseous dental implant made of titanium enjoys sufficient predictable success to have become the artificial root most frequently chosen for restoring dentition to edentulous patients, but that success depends in part on the micromorphologic nature of the surface of the implant which comes in contact with the host bone. Because there is no standard for the surface micromorphology of dental implants, the surfaces of commercial implants have a wide range of available textures. It is known that osseointegration of dental implants is dependent, in part, on the attachment and spreading of osteoblast-like cells on the implant surface. It appears that such cells will attach more readily to rough surfaces than to smooth surfaces, but an optimum surface for long-term stability has not yet been defined.

Wilke, H. J. et at. have demonstrated that it is possible to influence the homlding power of implants by altering surface structure morphology: "The Influence of Various Titanium Surfaces on the Interface Strength between Implants and Bone", *Advances in Biomaterials*, Vol. 9, pp. 309–314, Elsevier Science Publishers BV, Amsterdam, 1990. While showing that increased surface roughness appeared to provide stronger anchoring, these authors comment that it "cannot be inferred exclusively from the roughness of a surface as shown in this experiment. Obviously the shear strength is also dependent on the kind of roughness and local dimensions in the rough surface which can be modified by chemical treatment."

Buser, D. et at., "Influence of Surface Characteristics on Bone Integration of Titanium Implants", *Journal of Biomedical Materials Research*, Vol. 25, pp. 889–902, John Wiley & Sons, Inc., 1991, reports the examination of bone reactions to titanium implants with various surface characteristics to extend the biomechanical results reported by Wilke et al. The authors state that smooth and titanium plasma sprayed ("TPS") implant surfaces were compared to implant surfaces produced by alternative techniques such as sandblasting, sandblasting combined with acid treatment, and plasma-coating With HA. The evaluation was performed with histomorphometric analyses measuring the extent of the bone-implant interface in cancellous bone. The authors state, "It can be concluded that the extent of bone-implant interface is positively correlated with an increasing roughness of the implant surface."

Prior processes that have been used in attempts to achieve biocompatible surfaces on surgically implantable prosthetic devices have taken many forms, including acid etching, ion etching, chemical milling, laser etching, and spark erosion, as well as coating, cladding and plating the surface with various materials, for example, bone-compatible apatite materials such as hydroxyapatite or whitlockite or bone-derived materials. Examples of U.S. patents in this area are U.S. Pat. No. 3,855,638 issued to Robert M. Pilliar Dec. 24, 1974 and U.S. Pat. No. 4,818,559 issued to Hama et at. Apr. 04, 1989. A process of ion-beam sputter modification of the surface of biological implants is described by Weigand, A. J. et al. in *J. Vac. Soc. Technol.*, Vol. 14, No. 1, Jan/Feb 1977, pp. 326–331.

As Buser et al. point out (Ibid p. 890), the percentage of bone-implant contact necessary to cream sufficient anchorage to permit successful implant function as a load-bearing device over time remains unclear. Likewise, Wennerberg et al., "Design and Surface Characteristics of 13 Commercially Available Oral Implant Systems", *Int. J. Oral Maxillofacial Implants* 1993, 8:622–633, show that the different implants studied varied considerably in surface topography, and comment: "Which of the surface roughness parameters that will best describe and predict the outcome of an implant is not known" (p. 632).

Radio-frequency glow-discharge treatment, also referred to as plasma-cleaning ("PC") treatment, is discussed in Swart, K. M. et at., "Short-term Plasma-cleaning Treatments Enhance in vitro Osteoblast Attachment to Titanium", *Journal of Oral Implantology*, Vol. XVIII, No. 2 (1992), pp. 130–137. These authors comment that gas plasmas may be used to strip away organic contaminants and thin existing oxides. Their conclusions suggest that short-term PC treatments may produce a relatively contaminant-free, highly wettable surface. U.S. Pat. No. 5,071,351, issued Dec. 10, 1991, and U.S. Pat. No. 5,188,800, issued Feb. 23, 1993, both owned by the assignee of the present application, describe and claim methods and means for PC cleaning of a surgical implant to provide a contact angle of less than 20 degrees.

Copending application Ser. No. 08/149,905, filed Nov. 10, 1993, owned by the assignee of the present application, describes and claims inventions for improving the surfaces of surgically implantable devices which employ, among other features, impacting the surface with particles of the same material as the device to form the surface into a desired pattern of roughness.

SUMMARY OF THE INVENTION

It is a primary object of the present invention to produce an implant surface having a roughness that is substantially uniform over the area of the implant that is intended to bond to the bone in which the implant is placed.

It is a further object of this invention to provide an improved surgically implantable device having on its surface a substantially uniform micromorphology.

It is another object of the invention to provide a process or processes for manufacturing such improved implant devices.

It is an additional object of the invention to provide such improved implant devices which can be manufactured without contaminating the surfaces thereof.

It is a more specific object of the invention to provide an improved etch-solution process that will result in a substantially uniform surface topography on surgically implantable devices.

In accordance with the present invention, the foregoing objectives are realized by removing the native oxide layer from the surface of a titanium implant, and then performing further treatment of the resulting surface substantially in the absence of unreacted oxygen. The further treatment preferably comprises acid etching the surface remaining after removal of the native oxide layer. The surface of the implant is also preferably grit blasted prior to removal of the native oxide layer. To enhance the bonding of the implant to the bone in which it is implanted, a bone-growth-enhancing material, such as bone minerals, hydroxyapatite, whitlockite, or bone morphogenic proteins, may be deposited on the treated surface. The implant is preferably maintained in an oxygen-free environment following removal of the native oxide layer, in order to minimize the opportunity for oxide to re-form before the subsequent treatment is performed.

DETAILED DESCRIPTION OF THE PREFERRED EMBODIMENTS

Figure 1:
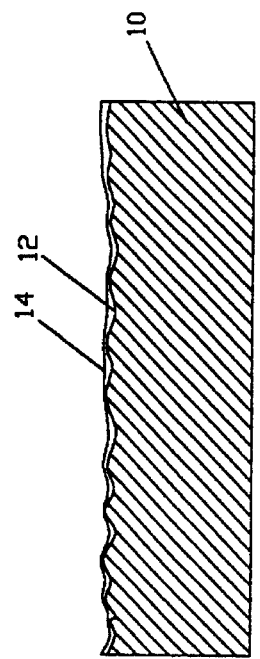
FIG. 1 is a diagrammatic sectional view taken through a body of titanium covered with a layer of native oxide.

Turning now to the drawings, and referring first to FIG. 1, a titanium body 10 which has been exposed to air has on its outer surface 12 an irregular layer 14 of an oxide or oxides of titanium which form naturally. This oxide layer 14 is referred to herein as the "native oxide" layer, and typically has a thickness in the range from about 70 to about 150 Angstroms. The native oxide layer that forms naturally on titanium when it is exposed to air is actually a combination of different oxides of titanium, including $TiO$, $TiO_2$, $Ti_2O_3$ and $Ti_3O_4$. The concentration of these oxides in the titanium body diminishes with distance from the surface of the body. The oxide concentration may be measured in an Auger spectrometer.

Auger electron spectroscopy (AES) measures the energy of Auger electrons produced when an excited atom relaxes by a radiationless process after ionization by a high energy electron, ion or x-ray beam. The spectra of a quantity of electrons emitted as a function of their energy reveal information about the chemical environment of the tested material. One of the major uses of AES is the depth profiling of materials, to reveal the thickness (depth) of the oxide layer on the surfaces of materials. These Auger electrons lie in an energy level that extends generally between the low energy level of the emission of secondary electrons up to the energy of the impinging electron beam. In this region, small peaks will occur in the spectra at certain energy levels that identify the existence of certain elements in the surface.

Figure 7:
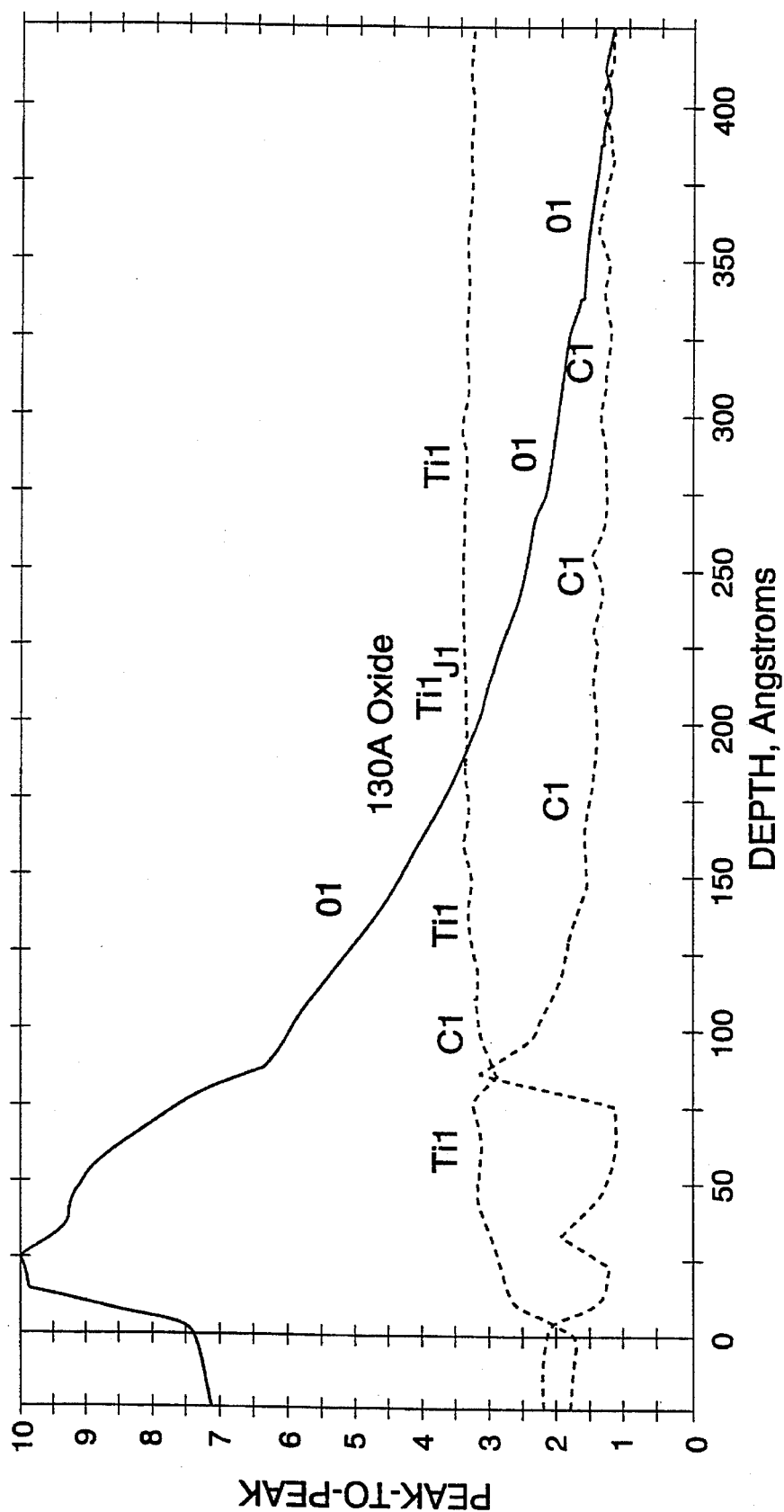
FIG. 7 is a graph of the results of an Auger electron spectroscopic analysis of a titanium surface that has been exposed to air.

As used herein, the term "native oxide layer" refers to the layer which extends from the surface of the material to the depth at which the energy of the peak-to-peak oxygen profile as measured in an Auger electron spectrometer decreases by one-half. For example, in the peak-to-peak oxygen profile reproduced in FIG. 7, the thickness of the native oxide layer was 130 Angstroms, which is the depth at which the oxygen profile dropped to half its maximum intensity. Thus, removal of a 130 Angstrom layer from the surface of the titanium body would remove the native oxide layer.

Figure 2:
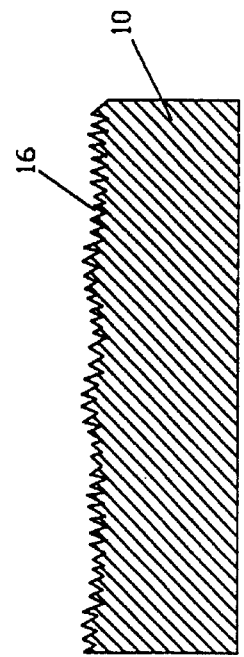
FIG. 2 is the same section shown in FIG. 1 after impacting the surface with a grit.

FIG. 2 depicts the surface 12 of the titanium body 10 after being grit blasted to achieve initial toughening, as described in more detail below. The oxide layer 14 is still present, but it has a rougher surface than in its original state depicted in FIG. 1.

Figure 3:
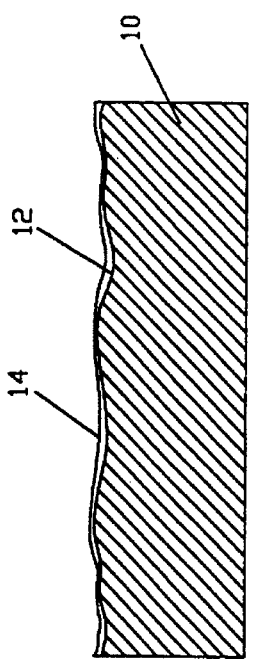
FIG. 3 is the same section shown in FIG. 2 after bulk etching with an acid etch.

FIG. 3 depicts the grit-blasted surface 12 of the titanium body 10 after it has been bulk etched in an etching acid. The etched area 16 where the native oxide layer 14 has been removed by the etching acid exhibits a much finer roughness, but in areas where the oxide layer remains, the initial roughness depicted in FIG. 2 also remains.

Figure 4:
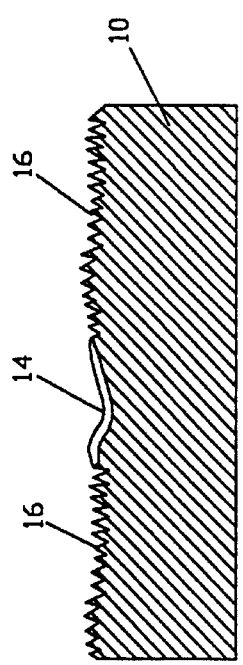
FIG. 4 is the same section shown in FIG. 2 after first removing the native oxide and then bulk etching with an acid.
Figure 5A:
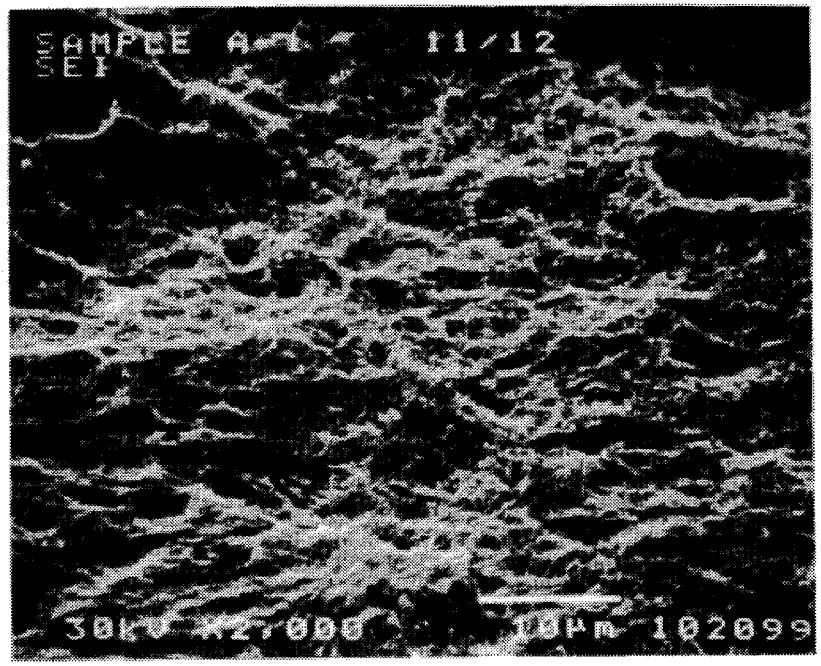
FIGS. 5A and 5B are scanning electron micrographs ("SEMs") of two titanium dental implants prepared in accordance with the present invention.
Figure 5B:
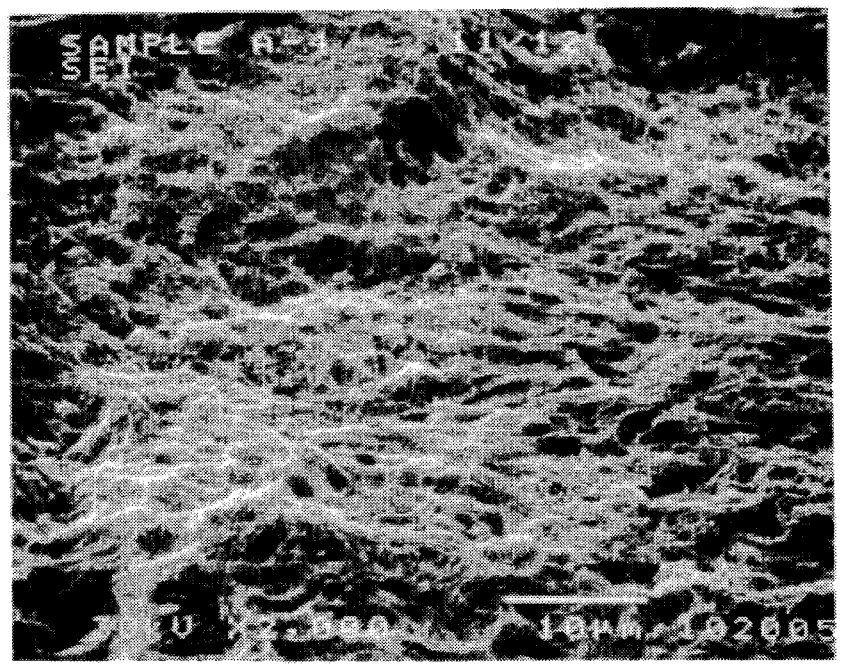
Figure 6A:
FIGS. 6A and 6B are SEMs of the same implants shown in FIGS. 5A and 5B, at a higher magnification level.
Figure 6B:
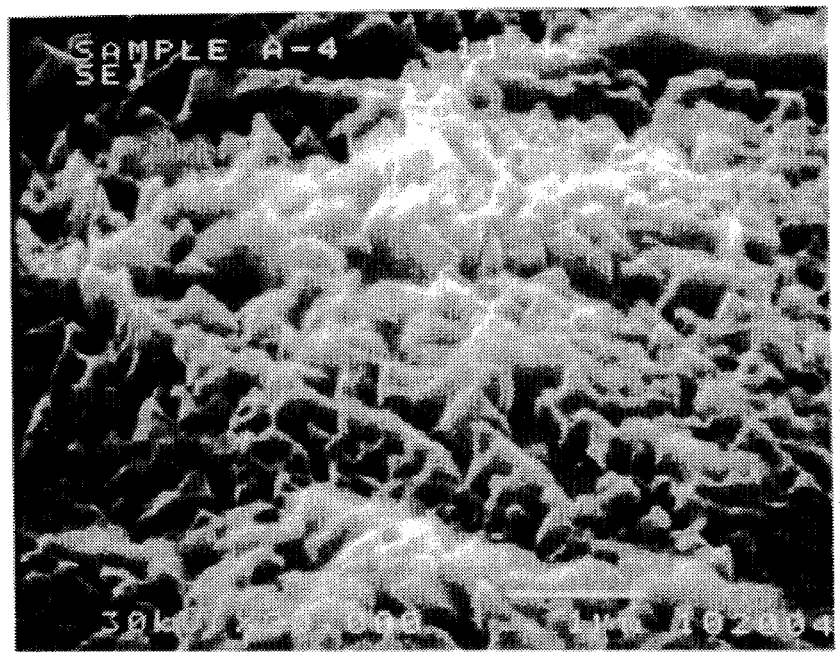

FIG. 4 depicts the grit-blasted surface 12 of the titanium body 10 after it has been etched in a first acid to remove the native oxide layer 14, and then in a second acid to produce the desired topography on the surface 16 produced by the first acid treatment. As described in more detail below, the preferred surface topography has a substantially uniform free roughness over the entire surface 16.

Among the processes previously used to improve the surfaces of dental implants made of titanium is that of etching the surface with an acid, such as a mixture of two parts (by volume) sulfuric acid and one part (by volume) muriatic acid. It has been found that such acid treatments do not etch the implant surface uniformly or consistently from one region to another.

According to one aspect of the present invention, the native oxide layer is removed from the surface of a titanium implant prior to the final treatment of the surface to achieve the desired topography. After the native oxide layer is removed, further treatment of the surface is preferably carried out in the absence of unreacted oxygen to prevent the oxide layer from re-forming until after the desired surface topography has been achieved. It has been found that this process permits the production of unique surface conditions that are substantially uniform over the implant surface that is so treated.

Removal of the native oxide layer can be effected by immersing the titanium implant in an aqueous solution of hydrofluoric (HF) acid at room temperature. A preferred concentration for the hydrofluoric acid used in this oxide removal step is 15% $HF/H_2O$. This concentration produces an etch rate of approximately 200–350 Angstroms per minute at room temperature, without agitation, so that a typical native oxide layer having a thickness in the range from about 70 to about 150 Angstroms can be removed in about one-half minute. Other suitable etching solutions for removing the native oxide layer, and their respective etch rates, are:

50% HF—etch rate~600 to 750 Angstroms/min.

30% HF—etch rate~400 to 550 Angstroms/min.

10% HF—etch rate~100 to 250 Angstroms/min.

A 100% HF was found to be difficult to control, and the etch rate was not determined. The preferred 15% HF solution allows substantially complete removal of the native oxide layer with minimum further consumption of the titanium surface after the implant is removed from the solution.

Prior to removing the native oxide layer, it is preferred to grit blast the oxide-bearing surface, preferably with grit made of titanium or a dilute titanium alloy. As is taught in the aforementioned copending U.S. patent application Ser. No. 08/149,905, the use of a grit made of titanium avoids contaminating the surface of a titanium implant. Thus, for a dental implant made of commercially pure ("CP") titanium, the blasting material may be CP B299 SL grade titanium grit. The preferred particle size for this grit is in the range from about 10 to about 60 microns (sifted), and the preferred pressure is in the range from about 50 to about 80 psi.

The grit blasting of the titanium surface prior to the acid treatments appears to accelerate the etching of the metal by the acids, and also contributes to the unique topography of the final etched surface. This topography is described in more detail below.

The surface treatment that follows removal of the native oxide layer from the implant surface may take several forms, singly or in combination. The preferred treatment is a second acid etching step, using an etch solution consisting of a mixture of two parts 95.5% sulfuric acid in water and one part 31.45% muriatic acid in water ("Modified Muriaticetch") at room temperature. This mixture provides a sulfuric acid/hydrochloric acid ratio of about 6:1. This preferred etch solution is controllable, allowing the use of bulk etch times in the range from about 3 to about 10 minutes. This solution also can be prepared without the risk of violent reactions that may result from mixing more concentrated HCl solutions (e.g., 98%) with sulfuric acid. This second etching treatment is preferably carried out in the absence of unreacted oxygen, and before the implant surface has been allowed to re-oxidize, following removal of the native oxide layer. Of course, the implants may be kept in an inert atmosphere between the two etching steps.

The second etching step produces a surface topography that includes many fine cone-like structures in the sub-micron size range. Because of the fine roughness of the surface, and the high degree of uniformity of that roughness over the treated surface, this surface provides a good site for the application of various materials that can promote bonding of the surface to adjacent bone. Examples of such materials are bone-growth-enhancing materials such as bone minerals, bone morphogenic proteins, hydroxyapatite, whitlockite, and medicaments. These materials are preferably applied to the etched surface in the form of free particles which become entrapped on and between the small cone-like structures. The bone-growth-enhancing materials are preferably applied in the absence of oxygen, e.g., using an inert atmosphere.

The roughness of the surface to which these materials are applied enhances the adherence of the applied material to the titanium implant. The uniformity of the rough surface enhances the uniformity of the distribution of the applied material, particularly when the material is applied as small discrete particles or as a very thin film.

A preferred natural bone mineral material for application to the etched surface is the mineral that is commercially available under the registered trademark "BIO-OSS". This material is a natural bone mineral obtained from bovine bone; it is described as chemically comparable to mineralized human bone with a fine, crystalline biological structure, and able to support osseointegration of titanium fixtures.

The invention will be further understood by reference to the following examples, which are intended to be illustrative and not limiting:

EXAMPLE NO. 1

A batch of 30 screw-type cylindrical implants made of CP titanium were grit blasted using particles of CP B299 SL grade titanium grit having particle sizes ranging from 10 to 45 microns, at a pressure of 60 to 80 psi. After grit-blasting, native oxide layer was removed from the implant surfaces by placing 4 implants in 100 ml. of a 15% solution of HF in water at room temperature for 30 seconds. The implants were then removed from the acid, neutralized in a solution of backing soda, and placed in 150 ml. of "Modified Muriaticetch" (described above) for 3 minutes. The implants were then removed from the acid, neutralized, rinsed cleaned. All samples displayed very similar surface topographies and a high level of etch uniformity over the surface, when compared with each other in SEM evaluations. Consistency in the surface features (peaks and valleys) was also observed. The SEMs in FIGS. 5A, 5B, 6A and 6B show the surface of two of the implants, Sample A-1 and Sample A-4, at magnifications of 2,000 and 20,000. It will be observed that the surface features over the area shown are consistent and uniform. The scale shown on the ×20,000 photographs is 1 micron=0.564 inch. At this magnification the surface appear to be characterized by two-dimensional array of cones ranging in height (as seen in the SEMs) from about 0.17 inch to about 0,27 inch; the base diameters of these cones varied from about 0.17 inch to about 0.33 inch. Converting these numbers to metric units on the above-mentioned scale (1 micron=0,564 inch) yields:

cone height range (approx.)=0.30 to 0.50 micron cone base diameter range (approx.)=0.30 to 0.60 micron.

The same degree of uniformity was found in all the samples, and from sample to sample, at magnifications of 2,000 and 20,000, as compared with similar samples subjected to bulk etching without prior removal of the native oxide, as described in EXAMPLE NO. 2 below.

EXAMPLE NO. 2

Four of the implants that had been grit blasted as described in EXAMPLE NO. 1 above were placed in 150 ml. of "Modified Muriaticetch" for 10 minutes. The implants were then removed, neutralized, rinsed and cleaned. SEM photographs taken at magnifications of 2,000 and 20,000 showed that the bulk etch solution failed to remove the native oxide layer after 10 minutes in the etch solution. The failure to remove the native oxide layer (100–150 Angstrom units thick) resulted in a non-uniformly etched surface, as depicted in FIG. 3. In areas of the implant surfaces where the native oxide was removed, the topography was similar to that observed on the implants in EXAMPLE NO. 1.

I claim:

1. A method of preparing the surface of a device that is surgically implantable in living bone and that is made of titanium having a native oxide layer on the surface thereof, said method comprising the steps of grit blasting the surface of said device to roughen the surface, etching the grit blasted surface with hydrofluoric acid to remove the native oxide layer, and etching the resulting surface with a mixture of sulfuric and hydrochloric acids to produce a uniformly roughened surface.

2. The method of claim 1 wherein the ratio of sulfuric acid to hydrochloric acid in said aqueous solution is approximately 6 to 1.

3. The method of claim 1 wherein said acid etching is carried out at room temperature.

4. The method of claim 1 wherein said hydrofluoric acid is in an aqueous solution that produces an etch rate of from about 200 to about 350 Angstroms per minute.

5. The method of claim 1 which includes the step of depositing on the acid-etched surface at least one material selected from the group consisting of bone minerals, hydroxyapatite, whitlockite, bone morphogenic proteins and medicaments.

6. The method of claim 5 wherein said deposited material is in particulate form.

7. The method of claim 5 wherein said depositing step is carried out substantially in the absence of oxygen.

8. The method of claim 1 wherein the grit used in said grit blasting is composed of titanium or a dilute alloy of titanium.

9. The method of claim 1 wherein the grit used in said grit blasting has a particle size of from about 10 to about 60 microns.

10. The method of claim 1 wherein said grit blasting is carrted out at a pressure of from about 50 to about 80 psi.

11. A method of preparing the surface of a dental implant made of titanium having on the surface thereof a native oxide layer having a thickness between about 70 and about 150 Angstroms, said method comprising the steps of removing the native oxide layer from the surface of the implant by immersing the implant in hydrofluoric acid of sufficient strength to etch the native oxide layer at a rate of at least 100 Angstroms per minute, removing the implant from the hydrofluoric acid after removal of the native oxide layer, and before re-oxidation of the etched surface, immersing the implant in a mixture of sulfuric acid and hydrochloric acid for about 3 to about 10 minutes to produce a uniformly etched surface.

12. The method of claim 11 wherein the ratio of sulfuric acid to hydrochloric acid in said aqueous solution is approximately 6 to 1.

13. The method of claim 11 which further includes the step of depositing on the acid-etched surface at least one material selected from the group consisting of bone minerals, hydroxyapatite, whitlockite, bone morphogenic proteins and medicaments.

14. The method of claim 13 wherein said depositing step is carrted out substantially in the absence of oxygen.

15. The method of claim 11 which further includes the step of grit blasting the implant surface prior to removal of the native oxide layer.

* * * * *